United States Patent [19]

Gansow et al.

[11] 4,454,106

[45] Jun. 12, 1984

[54] USE OF METAL CHELATE CONJUGATED MONOCLONAL ANTIBODIES

[76] Inventors: Otto A. Gansow, 3003 Van Ness, NW., Washington, D.C. 20008; Mette Strand, 807 Harper House, Baltimore, Md. 21210

[21] Appl. No.: 386,109

[22] Filed: Jun. 7, 1982

[51] Int. Cl.$^3$ .................. G01N 33/60; A61K 43/00; A61K 49/02

[52] U.S. Cl. ...................................... 424/1.1; 424/9; 436/548; 436/73; 436/74; 436/84; 436/804; 436/819; 128/1.1; 128/659

[58] Field of Search .................. 436/547, 548, 73–74, 436/84, 81, 804, 819; 424/1, 1.5, 1.1, 9; 128/1.1, 659, 665; 435/68, 70, 172

[56] References Cited

U.S. PATENT DOCUMENTS

| | | | |
|---|---|---|---|
| 3,961,038 | 6/1976 | Benes | 424/1 |
| 4,196,265 | 4/1980 | Koprowski et al. | |
| 4,283,382 | 8/1981 | Frank et al. | 424/8 |
| 4,311,688 | 1/1982 | Burchiel et al. | 424/1 |
| 4,323,546 | 4/1982 | Crockford et al. | 424/1.5 |
| 4,331,647 | 5/1982 | Goldenberg | |
| 4,339,426 | 7/1982 | Meares et al. | 424/1 |
| 4,348,376 | 9/1982 | Goldenberg | |
| 4,361,544 | 11/1982 | Goldenberg | 424/1 |
| 4,364,920 | 12/1982 | Winchell | 424/1 |

FOREIGN PATENT DOCUMENTS 38546 10/1981 European Pat. Off. .
66786 12/1982 European Pat. Off. .

OTHER PUBLICATIONS

Pritchard, J. H. et al., Proc. Soc. Experiment. Biology and Medicine, vol. 151, pp. 297–302, (1976).
Scheinberg et al., Science, vol. 215, pp. 1511–1513, (3-19-1982).
Khaw, B. A. et al., Science, vol. 209, p. 295, (1980).
Scheinberg et al., Monoclonal Antibodies in Drug Development, Amer. Soc. Pharm. Exp. Therap., (1981), (Applicants).
Scheinberg et al., "Leukemic Cell Targeting and Therapy by Monoclonal Antibody in a Mouse Model System," (1982), *Cancer Research* 42: 44–49.
Scheinberg et al., "Targeting in Erytholeukemic Mice: Radioiodinated and Chelated Radiometal-Conjugated Monoclonal Antibody," in *Monoclonal Antibodies in Drug Development*, pp. 159–171, (J. T. August ed. 1982).
Hnatowich et al., *Int'l. J. App. Radiat. Isot.*, 33: 326–332, (1982).
Scheinberg et al., *Science*, 215: 1151–1153, (1982).
Paik et al., *J. Nuc. Med.*, 22: 32 (1981).
Krejcarek et al., *Biochem. Biophys. Res. Commun.*, 77: 581 (1977).
Meares et al., *Proc. Natl. Acad. Sci. USA*, 73: 3803–3806, (1976).
Paik et al., *J. Radioanal. Chem.*, 57: 553–564, (1980).
Bloomer et al., *Science*, 212: 340–341, (1981).
Zucchini et al., *Int. J. Nucl. Med. & Biol.*, 9: 83–84, (1982).

*Primary Examiner*—Benjamin R. Padgett
*Assistant Examiner*—M. Moskowitz
*Attorney, Agent, or Firm*—Banner, Birch, McKie & Beckett

[57] ABSTRACT

Therapeutic and diagnostic methods employing metal chelate conjugated monoclonal antibodies are described. Metals employed in therapeutic conjugated antibodies include alpha particle, beta particle or Auger electron emitting isotopes. Diagnostic methods may be either in vivo or in vitro. Chelated metals employed in diagnostic techniques may include, inter alia, gamma or positron emitting metals as well as fluorogenic or paramagnetic metals.

21 Claims, No Drawings

USE OF METAL CHELATE CONJUGATED MONOCLONAL ANTIBODIES

TECHNICAL FIELD

This invention relates generally to metal chelate conjugated monoclonal antibodies. In one aspect, this invention relates to a method for treating cellular disorders, particularly cancer, which employs a radiometal chelate conjugated monoclonal antibody. In another aspect it relates to the use of metal chelate conjugated monoclonal antibodies for diagnostic purposes.

BACKGROUND OF THE INVENTION

Effective therapeutic methods for the treatment of cellular disorders such as cancer have been the object of intensive research. Conventional therapy employs surgery, radiation and chemotherapy. Each of these methods suffers a serious drawback in that it is not highly selective between healthy and cancerous cells. In order to be effective, these methods kill or remove large amounts of healthy tissue. Furthermore, chemotherapy adversely affects the immune system so that death or serious illness often arises from fungal, bacterial or viral infections.

The development of monoclonal antibodies has opened the possibility of selectively delivering therapeutic agents or diagnostic agents to specific target cells. Monoclonal antibodies are immunoglobulins of well-defined chemical structure. A characteristic feature of monoclonal antibodies is reproducability of function and high specificity.

Radioiodine bound directly to monoclonal antibodies has been used for diagnosis and therapy. Iodine-131 has had some therapeutic success for large tumors, but radioiodine labled antibodies have been ineffective in the treatment of small tumor foci or metastases. In addition, specifically bonded antibodies are relatively rapidly catabolized by the target cell. Catabolism, therefore, leads to the incorporation of metabolized iodine in the excretory organs, i.e., kidney, bladder and stomach. In addition, attempts to transport toxins via monoclonal antibodies to tumor cells have not resulted in a successful therapeutic method.

It has been suggested in the literature that diethylenetriaminepentaacetic acid (DTPA) can form stable metal complexes when attached to protein. Krejcarek et al., 77 *Biochem. & Biophys. Res. Commun.* 581 (1977). Imaging of target sites in vivo with radiometal-DTPA conjugated polyclonal antibodies prepared according to the method of Krejcarek have been reported by Khaw et al., 209 *Science* 295 (1980). Despite separation, by gel chromatography and dialysis, of free and chelated metal from metal chelate conjugated polyclonal antibodies the gamma images included in the article show that a high proportion of the radiometal localized in the liver.

Diagnostic methods are adversely affected unless substantially all of the compound used for labeling is attracted to the desired target. Any of the labeling compound that does not attach to the target can create an undesirable background. If radiometals are used, they can disseminate in the body and have the potential of doing damage.

SUMMARY OF THE INVENTION

It is an object of the present invention to provide improved therapeutic and diagnostic methods.

It is another object of the present invention to provide an effective method of treating cellular disorders employing monoclonal antibodies.

It is a further object of the present invention to provide a method of selectively targeting lethal doses of radiation to diseased cells which causes little or no destruction of healthy cells.

It is a still further object of the present invention to provide a method of selectively treating small tumor foci and metastases.

It is also an object of the present invention to provide a diagnostic method employing metals which localize at target sites.

It is another object of the present invention is to provide a method of introducing selectively targeted radiometals in vivo which avoids appreciable radiometal incorporation into healthy organs of the body.

In one of its aspects, the present invention provides a method of treating cellular disorders comprising contacting a target cell with radiometal chelate conjugated monoclonal antibodies wherein said radiometal is an alpha particle, beta particle or Auger electron emitting metal nuclide. In another embodiment, the present invention contemplates a method comprising introducing into body fluid metal chelate conjugated monoclonal antibodies wherein said conjugated chelate is a derivative of diethylenetriaminepentaacetic acid, said conjugate being substantially free of adventitiously bound ions of said metal and retaining substantially all of the activity and selectivity of the antibody. Such a technique is suitable for both diagnostic and therapeutic purposes.

DETAILED DESCRIPTION OF THE INVENTION

The present invention employs metal chelate conjugated monoclonal antibodies for diagnostic and therapeutic techniques, particularly in vivo. The metal may be radioactive, exhibit fluorogenic properties, exhibit paramagnetic properties or the like.

In one of its preferred aspects, the invention contemplates employing metal chelate conjugated monoclonal antibodies in which the chelate is derived from diethylenetriaminepentaacetic acid (DTPA), and the conjugate is substantially free of adventitiously bound metal. Moreover, the conjugates can retain substantially all of the activity and selectivity of the antibody. These conjugates have been found to be very useful, particularly for in vivo administration. The conjugates attach to the targets with little or no unwanted accumulation of metal in body organs such as the liver and spleen. This conjugate is suitable for either diagnostic or therapeutic use. For ease of presentation, the invention in all of its aspects will be described with respect to such DTPA chelate.

Monoclonal antibodies are immunogobulins of well-defined chemical structure, in contrast to polyclonal antibodies which are heterogeneous mixtures. Reproducability of function cannot be controlled for either polyclonal or autologus antibodies, whereas unaltered function is characteristic to monoclonal antibodies. Experimental techniques for obtaining monoclonal antibodies have been extensively discussed. A useful test is *Monoclonal Antibodies* (R. H. Kennett, T. J. McKearn & K. B. Bechtol eds. 1980). See also Koprowski et al. U.S. Pat. No. 4,196,265. Any monoclonal antibody which exhibits cell binding or antigen binding at the cell targeted for therapy can be employed. The selection and production of suitable monoclonal antibodies is within the skill of the art.

The antibodies are generally maintained in an aqueous solution that contains an ionic compound. A physiologic normal saline solution is very often employed and is widely available. Other ionic solutions, such as those containing sodium or potassium phosphate, sodium carbonate and the like, are known in the art and may also be employed.

Preferred methods for the preparation of metal (DTPA) conjugated monoclonal antibodies are described in detail in copending application entitled "Metal Chelate Conjugated Monoclonal Antibodies," Ser. No. 386,110, filed on even date herewith. Generally, the chelate conjugated to the monoclonal antibody is a derivative of DTPA bonded to an organic functional group which serves to link the DTPA chelate to the monoclonal antibody. Reacting the DTPA derivative and the monoclonal antibody produces the chelate conjugated monoclonal antibodies which can be reacted with a metal salt to produce the metal chelate conjugated monoclonal antibodies. By passing the resulting aqueous solution of the metal-containing conjugate through a column containing one or more ion exchange resins in addition to a sizing matrix, a metal DTPA conjugated monoclonal antibody solution is produced wherein at least about 94%, and desirably at least about 98%, of the metal is complexed in the DTPA chelate. While this invention is discussed in terms of metals or metal chelates, it will be understood that metal ions are, in fact, chelated in the conjugate. At least about 80%, and preferably at least about 95%, of the antibody activity and specificity can be retained by the conjugate.

The invention contemplates an in vivo therapeutic procedure in which radiometal chelate conjugated monoclonal antibodies are introduced into the body and allowed to concentrate in the target region. There are a wide variety of radiometal isotopes which form stable DTPA complexes and emit cytotoxic beta particles, Auger electrons and alpha particles. Useful beta particle emitting isotopes include Sc-46, Sc-47, Sc-48, Ga-72 and Ga-73. The therapeutic effect occurs when the conjugates are near or in contact with and bind to the targeted cells. Cell death, it is believed, is a direct or indirect result of the readiation event of the radiometal which is positioned in close proximity to the cell.

The benefits of this aspect of the invention are several. First, the high specificity of the conjugated monoclonal antibody minimizes the total radiation dosage. Only enough radiation for the target cells need be employed. In addition, radiometal chelates generally are cleared rapidly from the body should the conjugated antibody be disrupted. The isotope can be short-lived and the affinity constant by which the isotope is retained in the DTPA chelate is very high resulting in a stably bound metal. Finally, since the amount of radiometal employed is minimized, the radiation hazard to persons preparing and administering the radiometal chelate conjugated antibody is significantly reduced.

Because of the properties of the DTPA radiometal chelate conjugated monoclonal antibody employed by the present invention, tissue damage or whole body dose during therapy are markedly reduced as compared to that from presently employed methods of radiation therapy such as isotope implants, external radiation therapy, and immunoradiotherapy employing iodine-131 labeled polyclonal or autologus antibodies. Additionally, both biological and physical half-lives of the targeting radiobiological may now be controlled, minimizing whole body radiation effects. Since radiation is targeted specifically to cell types (e.g., neoplastic cells) a therapeutic dose is delivered specifically to malignant cells, either localized or metastasized. The ability of radiometal chelate conjugated monoclonal antibody to provide an effective dose of therepeutic radiation specifically to metastasized cells is also unique and singularly useful for cancer therapy.

In one of its particularly preferred aspects, the present invention employs the metal chelate conjugated monoclonal antibody containing an alpha emitting radiometal to treat cellular disorders. It is desirable in most applications that the radiometal have a half-life of less than about 4 days and decay rapidly to a stable isotope once the alpha particle is emitted. The preferred isotopes employed in the present invention are bismuth-211, bismuth-212, bismuth-213 and bismuth-214. Bismuth-212, with a half-life of 60.6 minutes, is particularly preferred.

The monoclonal antibody employed is specific for the diseased cell which is to be killed. Cell death is caused by decay of the radiometal and can occur in one of two ways. First, if the alpha particle is emitted in the direction of the diseased cell, a single hit in the cell nucleus can be cytotoxic. The isotope to which the radiometal decays after emitting the alpha particle is ejected from the chelate on a trajectory opposite that of the alpha particle. The bound cell, therefore, can still be hit even when the alpha particle is emitted on a trajectory away from the cell. A single hit in the cell membrane by the decayed isotope can cause irreparable cell injury leading to cell death. The relatively high effectiveness of the alpha particle means that less radioactive material can be employed. Selectivity of the monoclonal antibody and the short range (a few cell diameters) of the alpha particles minimizes the destruction of healthy tissue on a cellular level.

Bismuth-212 decays by one of two different pathways. Approximately 64% of the bismuth-212 decays via beta emission to polonium-212 which has a half-life of 0.3 microseconds. The polonium-212 decays to stable lead-208 after emitting an alpha particle with a range of approximately 90 microns. The other 36% of the bismuth-212 decays to thallium-208 by emitting an alpha particle with a range of approximately 35 to 50 microns. The thallium-208, with a half-life of 3 minutes, then decays via beta emission to stable lead-208.

Generators for Bi-212 have been described in the literature by Gleu, et al., 290 *Z. Anorg. Alleg. Chem.* 270 (1957), and by Zucchini, et al., *Int. J. Nucl. Med. & Biol.* (June, 1982), (the abstract of the manuscript was distributed at the August, 1981 ACS meeting in New York). A useful generator consists of Th-228 in the tetravalent state absorbed on a 3×5 mm bed of sodium titanate contained in a quartz column above a coarse fritted glass disc sealed in the column. The titanate tightly retains both Th-228 and its Ra-224 daughter. When water is passed through the titanate, the Rn-220 daughter of the Ra-224 isotope dissolves into the water and passes through the fritted disc and is collected in a 10 cc glass reservoir filled with water. The aqueous Rn-220 solution flows from the reservoir into a 10 mm diameter column containing approximately 1 ml of a strongly acidic ion exchange resin such as Bio-Rad AG-50 WX8 cation exchange resin. Rn-220 decays substantially within 5 minutes in the reservoir to Pb-212 which is absorbed upon passage through the resin. At flow rate of approximately 1.5 ml/min. through the resin, about 85% of the Pb-212 produced is collected in the column where it decays to its Bi-212 daughter.

When the desired amount of Bi-212 has been formed on the resin, it may be eluted by acid according to procedures entirely familiar to those skilled in the art. A useful method of elution for both Pb-212 and Bi-212 is to pass 5 ml of 2 N HCl through the resin. Alternatively, if only Bi-212 is desired, 1.5 ml of 0.5 M HCl can be passed through the resin.

While metals that emit beta particles or Auger electrons can be employed in the present invention, alpha emitting radiometals are preferred for several reasons. First, alpha nucleotide radiation characteristically has a short range in tissue and a very high linear energy transfer vis-a-vis beta or Auger radiation. Alpha radiation can kill a cell with only one hit to the nucleus and will kill substantially any cells with 10 hits or less. In addition, the decay also emits an isotope (e.g., Tl-208 or Pb-208 in the case of Bi-212) which can also cause cell death. The range of alpha particles is usually less than about 150 microns in tissue. In contrast, beta and Auger particles require hundreds of hits in the nucleus before causing cell death and have ranges in tissue on the order of tenths of millimeters to centimeters. When employing beta particles, a higher dose is required and the decay of substantially more radiolabeled antibodies will be needed to achieve cell death. Thus, specifically bound antibodies will be catabolized releasing beta emitting radiometals into the blood. Alpha-emitting radiometals kill relatively quickly so that fewer antibodies are catabolized.

Although the DTPA chelate conjugated monoclonal antibodies are preferred, this invention also contemplates the use of chelate conjugated monoclonal antibodies generally in conjunction with metal alpha, beta and Auger electron emitters for therapeutic use. A variety of chelates usefuel for conjugates with monoclonal antibodies are described in copending application Ser. No. 386,110, entitled "Metal Chelate Conjugated Monoclonal Antibodies" filed concurrently herewith.

In another embodiment, the present invention contemplates an in vivo diagnostic procedure which comprises introducing a metal chelate conjugated monoclonal antibody into the body, allowing sufficient time for the conjugate to localize and identifying the degree and location of localization, if any. The present invention also contemplates in vitro analytical procedures employing a chelate conjugated monoclonal antibody. The conjugated antibody of the present invention is substantially free of adventitiously or weakly chelated metal. The chelate conjugated to the antibody in the present invention is a derivative of diethylenetriaminepentaacetic acid (DTPA).

A wide variety of isotopes useful for diagnostic purposes form stable complexes with the DTPA chelate of the present invention. Gamma or positron emitting isotopes are particularly useful for imaging target sites both in vivo and in vitro. Examples of gamma or positron emitting isotopes include Tc-99m, Ga-67, Ga-68 or In-111. In the event that gamma camera images are desired, Tc-99m or In-111 are preferred. For positron emission tomography, Sc-43, Sc-44, Fe-52, Co-55 and Ga-68 may be employed. For fluorescence diagnostic techniques, lanthanides may be employed, in particular Pr, Nd, Sm, Eu, Gd, Tb, Dy, Ho, Er, Tm and Yb. Paramagnetic diagnostic techniques can would typically employ iron such as Fe-54, Fe-56, Fe-57 and Fe-58. Qualitative and quantative measurements can be made with instrumentation sensitive to each of these forms of emission, or properties (optical or magnetic), available in the art.

The metal chelate conjugated antibodies of this invention can be administered in vivo in any suitable pharmaceutical carrier. As noted earlier, a physiologic normal saline solution can appropriately be employed. Often the carrier will include a minor amount of carrier protein such as human serum albumin to stabilize the antibody. The concentration of metal chelate conjugated antibodies within the solution will be a matter of choice. Levels of 0.5 mg per ml are readily attainable but the concentrations may vary considerably depending upon the specifics of any given application. Appropriate concentrations of biologically active materials in a carrier are routinely determined in the art.

The effective dose of radiation or metal content to be utilized for any application will also depend upon the particulars of that application. In treating tumors, for example, the dose will depend, inter alia, upon tumor burden, accessability and the like. Somewhat similarly, the use of metal chelate conjugated antibodies for diagnostic purposes will depend, inter alia, upon the sensing apparatus employed, the location of the site to be examined and the like. In the event that the patient has circulating antigen in addition to those located at the site, the circulating antigens can be removed prior to treatment. Such removal of antigens can be accomplished, for example, by the use of unlabeled antibodies, or by plasmaphoresis in which the patient's serum is treated to remove antigens.

The following examples are included for illustrative purposes only and are not intended to limit the scope of the invention.

EXAMPLE I

One hundred milligrams of DTPA was weighed into a flask and to this was added 1 ml of water. This solution was reacted with 0.125 g redistilled triethylamine. The reaction solution was warmed to complete the reaction and a solid product was collected by freeze drying.

The freeze dried solid was dissolved in 0.5 ml of pure, dry acetonitrile and 35 ul isobutylchloroformate added at a temperature of approximately −20° C. and brought down to about −70° C. After about 45 minutes, the solution was centrifuged in an Eppendorf vial. The supernatant liquid was collected which contained the desired mixed carboxycarbonic anhydride of DTPA at a concentration of approximately 0.5 M.

The monoclonal antibody employed was designated 103A5 and was obtained by fusing P3X63Ag8 mouse myeloma cells with the isolated spleen cells of C56B1/6 mice which had been immunized with purified retrovirus glycoprotein of 70,000 daltons (gp70) obtained as described by M. Strand and J. T. August, 251 *J. Biol. Chem.* 559 (1976). The fusion was carried out as described by M. Strand, 77 *Proc. Natl. Acad. Sci. USA* 3234 (1980).

A 114 ul solution containing 2 mg of monoclonal antibody 103A5 in 0.1 M NaHCO$_3$ at a pH of approximately 7.2 and 150 mM sodium chloride was prepared and pipetted into a Nunc vial. Then, 33 ul of a 0.1 M NaHCO$_3$ solution at a pH of 7.0 was added to the vial. Finally, 26.4 ul of the mixed carboxycarbonic anhydride of DTPA (0.5 M in acetonitrile) was added after cooling the chelate and antibody solutions to approximately 0° C. The reaction was allowed to proceed overnight.

The product was first dialyzed at 4° C., against one liter of 30 mM ascorbic acid, 5 mM EDTA, 200 mM NaCl and 20 mM of sodium citrate (pH 7.0). The resulting solution was dialyzed at 4° C. against three one liter changes of 50 mM citrate, 200 mM sodium chloride at pH 6.0, and 1 ml Chelex 100 resin (Bio-Rad) over a 48 hour period. Finally, the resulting solution was dialyzed for 8 hours against one liter of a solution that had a concentration of 10 mM MES and 200 mM sodium chloride at pH 6.0. Approximately 1.7 mg of chelate conjugated monoclonal antibody was recovered. Analogous experiments employing C-14 labled DTPA were analyzed by scintillation counting and shown to contain approximately 1.5 chelates per antibody molecule.

Forty microliters of Indium-111 chloride solution (New England Nuclear Corp.) was adjusted to pH 3.0 by the addition of 11.4 ul of 0.4 M citric acid at pH 5.0. A separate solution was prepared containing 250 micrograms of chelate conjugated monoclonal antibody in a total volume of 21.6 microliters. The solution had a concentration of 200 mM sodium chloride and 10 mM MES at a pH of 6.0. The solution was adjusted to pH 4.6 by the addition of 6 ul of 0.25 M citric acid at a pH of 3.0.

The metal chelate conjugated monoclonal antibody was prepared by combining the indium chloride and chelate conjugated antibody solutions and allowing them to react for approximatley 30 minutes at ambient temperature. The reaction was terminated by adding 25 ul of a saturated solution of trisodium citrate to adjust the pH to about 6.

The chelate conjugated antibody was purified by chromatography on 9 cm long column containing 1.0 ml of an ion retardation resin (AG 11-A8 available from Bio-Rad) above 1.0 ml of a cation exchange resin (AG-50-WX8, H+ form, 200-400 mesh available from Bio-Rad) above 7 ml of Sephadex G-50 gel (Pharmacia). A solution with concentrations of 200 mM sodium chloride and 10 mM MES at a pH of 6.0 was used as the eluant and was used pre-equilibrate the column.

The eluate was collected in 0.5 ml fractions. The two fractions with most of the protein were shown to contain 150 ug of monoclonal antibody labeled with 157.1 microcuries Indium-111. Dialysis at 4° C. against one liter of an aqueous solution of 20 mM MES and 200 mM sodium chloride at pH 6.0 showed less than 6% loss of Indium. The antibody was shown to retain substantially 100% of its biological activity and specificity by in vitro tests. In vivo imaging in leukemic mice highlighted the tumor site in the spleen. When administered to normal mice there was no uptake by the spleen.

EXAMPLE II

A hybridoma was obtained by fusing P3 653 mouse myeloma cells with the isolated spleen cells of C56B1/6 mice which had been immunized with purified tumor-associated ferritin isolated from the human spleen. A hybridoma was isolated that produced an anti-ferritin antibody designated 263D5. The antibody was specific for human ferritin and did not react with ferritin of other mammalian species.

The procedure of Example 2 was repeated to provide an indium-111 containing DTPA conjugated monoclonal antibody. A physiologic normal saline solution containing the metal chelate conjugated monoclonal antibody was injected into normal and leukemic mice.

In both the leukemic and normal mice, radio imaging showed that there was no concentration of radio labeled metal. These tests demonstrated that the chelate was stable in vivo both with respect to the chelate-antibody conjugation and with respect to the retention of the radioactive metal. Neither the spleen nor the liver was highlighted in the images.

EXAMPLE III

Indium-111 chelate conjugated monoclonal antibodies were prepared from an antibody specific for human breast tumor. The hybridoma that produced the antibody was prepared from a fusion of mouse myeloma and mouse spleen cells. The hybridoma and antibody are described in 78 *Proc. Natl. Acad. Sci.* 3199 (1981).

The procedure employed was substantially the same as the procedures of Examples I and II, except for the following. First, the step of dialyzing the chelate conjugated monoclonal antibody against ascorbate-EDTA was omitted. Second, 10 microliters of 0.1 M ascorbate at pH 4 was added to the indium-111 solution prior its addition to the aqueous saline solution of the chelate conjugated monoclonal antibody.

The labeling efficiency exhibited a three-fold increase over the methods of Example I and II. The final product was labeled with approximately 2.1 microcuries per microgram.

Ten micrograms of the indium-111 chelated conjugated monoclonal antibody collected from the purification column was diluted to 100 microliters with an aqueous solution of phosphate buffered saline. The diluted indium-111 conjugated antibody was injected into the tail vein of a nude, athymic mouse in which a human breast tumor had been grown. The human breast tumor cells expressed an antigen for the antibody. Seventy-two hours after injection, a clear and well-defined gamma camera image demonstrated high localization of indium-111 in the tumor tissue. No similar localization of the indium-111 in the liver or spleen was observed.

Uses of the metal chelate conjugated monoclonal antibodies prepared according to this invention are described in more detail in copending application Ser. No. 386,110 entitled "Metal Chelate Conjugated Monoclonal Antibodies" filed concurrently herewith.

EXAMPLE IV

The following tables demonstrate that bismuth-DTPA chelate, as opposed to free bismuth, does not localize in the liver and spleen and is rapidly excreted through the kidneys and stomach. The uptake of radiometal into the organs of normal and leukemic mice was determined by the following procedure. Six-week old normal mice and mice made leukemic eight days previously by the injection of Rauscher leukemia virus were injected intraperitoneally with 5 micrograms (5 microcurie per microgram) of free Bi-207, DTPA chelated Bi-207 and DTPA chelated Sc-46. Eighteen and forty-two hours later, mice were sacraficed, their organs weighed, and the amount of radioactivity associated with the organs determined. In order to normalize for differences in the injections, in body weights, and in times of excising the organs, the amount of radioactivity per gram of tissue was divided by the amount of radioactivity per gram of blood, and results are expressed as this ratio. The results are shown in Tables 1, 2 and 3.

TABLE 1

MEANS AND STANDARD ERRORS OF THE MEAN
OF RATIO/BLOOD
OF 5 ORGANS OF 14-DAY LEUKEMIC AND
NORMAL MICE
AT 18 AND 42 HOURS AFTER INJECTION
OF FREE $^{207}$Bi$^a$.

| TISSUE | 18 HOURS LEUKEMIC | 18 HOURS NORMAL | 42 HOURS LEUKEMIC |
|---|---|---|---|
| HEART | 2.35 ± 0.65$^b$ | 4.0 ± 0.30 | 1.48 ± 0.12 |
| LIVER | 31.3 ± 7.50$^c$ | 29.0 ± 0.35 | 43.3 ± 2.65 |
| SPLEEN | 7.18 ± 2.03$^d$ | 21.1 ± 0.65 | 8.70 ± 0.66 |
| KIDNEY | 69.4 ± 43.7 | 612.6 ± 47.8 | 89.3 ± 9.18 |
| STOMACH | 1.35 ± 0.35 | 6.95 ± 0.65 | 5.01 ± 0.43 |

$^a$ = injected dose = 7 × 10$^6$ cpm per mouse
$^b$ = approximately 0.13% of total cpm in heart
$^c$ = approximately 40% of total cpm in liver
$^d$ = approximately 12% of total cpm in spleen

TABLE 2

MEANS AND STANDARD ERRORS OF THE MEAN
OF RATIO/BLOOD
OF 5 ORGANS OF LEUKEMIC AND NORMAL MICE
AT 18 HOURS
AFTER INJECTION WITH $^{207}$BI-DTPA CHELATE

| TISSUE | $^{207}$BI-DTPA$^a$ LEUKEMIC | $^{207}$BI-DTPA$^a$ NORMAL |
|---|---|---|
| HEART | 2.60 ± 0.33$^b$ | 2.45 ± 0.21 |
| LIVER | 19.12 ± 6.32$^c$ | 10.93 ± 1.24 |
| SPLEEN | 13.1 ± 2.6$^d$ | 12.4 ± 2.0 |
| KIDNEY | 294.0 ± 37.0 | 281.0 ± 26.0 |
| STOMACH | 7.52 ± 2.44 | 7.20 ± 2.90 |

$^a$ = injected dose 3.8 × 10$^6$ cpm per mouse
$^b$ = approximately 0.003% of total cpm in the heart
$^c$ = approximately 0.21% of total cpm in the liver
$^d$ = approximately 0.06% of total cpm in the spleen

TABLE 3

MEANS AND STANDARD ERRORS OF THE MEAN
OF RATIO/BLOOD
OF 5 ORGANS OF LEUKEMIC AND NORMAL
MICE AT 18 HOURS
AFTER INJECTION WITH $^{46}$BI-DTPA CHELATE

| TISSUE | $^{46}$SC-DTPA$^a$ LEUKEMIC | $^{46}$SC-DTPA$^a$ NORMAL |
|---|---|---|
| HEART | 3.66 ± 0.21$^b$ | 4.49 ± 0.84 |
| LIVER | 9.96 ± 0.57$^c$ | 7.23 ± 1.04 |
| SPLEEN | 3.17 ± 0.39$^d$ | 5.69 ± 0.28 |
| KIDNEY | 42.1 ± 0.9 | 29.5 ± 5.5 |
| STOMACH | 12.45 ± 5.43 | 7.76 ± 2.06 |

$^a$ = injected dose 5.4 × 10$^6$ cpm per mouse
$^b$ = approximately 0.006% of total cpm in the heart
$^c$ = approximately 0.14% of total cpm in the liver
$^d$ = approximately 0.08% of total cpm in the spleen The data in the above tables demonstrates that DTPA chelated bismuth and scandium do not concentrate in the liver of spleen of mice as opposed to free bismuth. High concentrations of chelated metal in the kidneys demonstrates that it is being voided through the urine. The variation in kidney concentrations between leukemic and normal mice is attributable to frequent voiding by the leukemic mice due to stress.

EXAMPLE V

Tests were conducted to determine the effect of bismuth alpha radiation on mammalian cells. F-46 leukemic cells were grown in vitro in Dulbacco's Modified Eagle medium containing 10% heat inactivated fetal calf serum to provide a cell population of 1 × 10$^5$ in each well. The cell populations were exposed to bismuth-212 by adding serial dilutions (as indicated in Table 4) in the growth medium. The cells were then grown for 96 hours and the number of surviving cells was determined. The results are shown in Table 4 below.

TABLE 4

| Dose (Rads) | Mean Number of Surviving cells (10$^5$) | Standard Deviation | % Survival |
|---|---|---|---|
| 0 | 6.9 | 1.4 | 100 |
| 0.2 | 8.0 | 0.5 | 116 |
| 0.4 | 6.1 | 1.7 | 88 |
| 0.8 | 6.7 | 1.4 | 97 |
| 1.5 | 6.0 | 2.8 | 87 |
| 3.1 | 6.0 | 0.6 | 87 |
| 6.2 | 5.0 | 0.6 | 72 |
| 12.3 | 2.9 | 0.4 | 42 |
| 24.6 | 2.2 | 0.4 | 32 |
| 49.2 | 1.1 | 0.4 | 16 |
| 98.4 | 0.6 | 0.1 | 9 |

From the above data of Table 4, employing standard calculation methods, $D_o$ (37% survival) is 38.5 rads. This demonstrates that bismuth-212 emits highly cytotoxic, densely ionizing radiation. By comparison, 900 rads of sparsely ionizing radiation from a cobalt-60 source was required to achieve the same results. For a discussion of radiation doses see: nm/mird pamphlets No's 1 (revised) and 10.

We claim:

1. A method of treating cellular disorders comprising introducing into body fluid a solution of radiometal chelate conjugated monoclonal antibodies specific for a target cell, said radiometal being an alpha, beta or Auger electron emitter and substantially all of said radiometal in said solution being chelated by said chelate conjugated monoclonal antibodies.

2. The method of claim 1 wherein the radiometal is an alpha emitter.

3. The method of claim 2 wherein said radiometal is selected from the group consisting of Bi-211, Bi-212 and Bi-213.

4. The method of claim 3 wherein said radiometal is Bi-212.

5. The method of claim 1 wherein said chelate is a derived from diethylenetriaminepentaacetic acid.

6. The method of claim 2 wherein said chelate conjugated monoclonal antibodies are produced from a carboxycarbonic anhydride of diethylenetriaminepentaacetic acid and a monoclonal antibody.

7. The method of claim 6 wherein said carboxycarbonic anhydride is produced form isobutylchloroformate and an amine salt of diethylenetriaminepentaacetic acid.

8. The method of claim 5 wherein said radiometal chelate conjugated monoclonal antibody solution has at least about 94% of the radiometal bound by the chelate and said conjugate retains at least about 80% of the biological activity and specificity of the antibody.

9. The method of claim 6 wherein said radiometal is Bi-212 and the metal chelate conjugated monoclonal antibody solution has at least about 98% of the radiometal bound by the chelate and said conjugate retains at least about 95% of the biological activity and specificity of the antibody.

10. A method of treating cellular disorders comprising introducing into body fluid a solution of radiometal diethylenetriaminepentaacetic acid chelate conjugated monoclonal antibodies wherein said radiometal is selected from the group consisting of beta emitting radiometals and Auger emitting radiometals, at least about 94% of said radiometal being bound by said chelate, and said conjugate having at least about 80% of the biological activity and specificity of the antibody.

11. The method of claim 10 wherein said radiometal is selected from the group consisting of Sc-46, Sc-47, Sc-48, Ga-72 and Ga-73.

12. The method of claim 10 wherein said conjugated antibody is produced from a carboxycarbonic anhydride of diethylenetriaminepentaacetic acid and a monoclonal antibody.

13. The method of claim 12 wherein said carboxycarbonic anhydride is produced from isobutylchloroformate and an amine salt of diethylenetriaminepentaacetic acid.

14. The method of claim 10 wherein at least about 98% of the radiometal is bound by the chelate and said conjugate retains at least about 95% of the biological activity and specificity of the antibody.

15. An in vivo diagnostic method comprising introducing into body fluid a solution of metal diethylenetriaminepentaacetic acid chelate conjugated monoclonal antibodies wherein said metal is selected from the group consisting of paramagnetic metals, gamma emitting metals and positron emitting metals, at least about 94% of said metal is bound by said chelate, and said conjugate has at least about 80% of the biological activity and selectivity of the antibody.

16. The method of claim 14 wherein said metal is selected from the group consisting of Tc-99m, In-111, Ga-67, Ga-68, Sc-43, Sc-44, Fe-52, Fe-54, Fe-56, Fe-57, Fe-58 and Co-55.

17. The method of claim 15 wherein at least about 98% of the radiometal is bound by the chelate and said conjugate retains at least about 95% of the biological activity and specificity of the antibody.

18. An in vitro diagnostic method comprising introducing into a test medium a solution of metal diethylenetriaminepentaacetic acid chelate conjugated monoclonal antibodies and quantifying the specifically bound portion of said conjugate, said metal being selected from the group consisting of fluorescent metals, paramagnetic metals, gamma emitting metals, positron emitting metals and beta emitting metals, at least about 94% of said metal being bound by said chelate, and said conjugate having at least about 80% of the biological activity and specificity of the antibody.

19. The method of claim 18 wherein said metal is selected from the group consisting of Tc-99m, In-111, Ga-67, Ga-68, Sc-43, Sc-44, Fe-52, Fe-54, Fe-56, Fe-57, Fe-58, and Co-55.

20. The method of claim 18 wherein said metal is selected from the group consisting of Pr, Nd, Sm, Eu, Gd, Tb, Dy, Ho, Er, Tm and Yb.

21. The method of claim 18 wherein at least about 98% of the radiometal is bound by the chelate and said conjugate retains at least about 95% of the biological activity and specificity of the antibody.

* * * * *

UNITED STATES PATENT AND TRADEMARK OFFICE
CERTIFICATE OF CORRECTION

PATENT NO. : 4,454,106

DATED : June 12, 1984

INVENTOR(S) : Otto A. Gansow and Mette Strand

It is certified that error appears in the above-identified patent and that said Letters Patent is hereby corrected as shown below:

At column 1, line 4, insert --This invention was made under a grant or award from the Department of Health and Human services At column 11, line 28, replace "14" with --15--.

At column 12, line 4, replace "the radiometal" with --said metal--.

At column 12, line 26, replace "the radiometal" with --said metal--.

Signed and Sealed this

Twentieth Day of November 1984

[SEAL]

Attest:

GERALD J. MOSSINGHOFF

Attesting Officer

Commissioner of Patents and Trademarks